United States Patent
King et al.

[11] Patent Number: 6,122,396
[45] Date of Patent: Sep. 19, 2000

[54] METHOD OF AND APPARATUS FOR AUTOMATING DETECTION OF MICROORGANISMS

[75] Inventors: Chester F. King; Robert A. Hallowitz, both of Frederick, Md.

[73] Assignee: Bio-Tech Imaging, Inc.

[21] Appl. No.: 09/376,052

[22] Filed: Aug. 17, 1999

Related U.S. Application Data

[63] Continuation-in-part of application No. 08/767,023, Dec. 16, 1996.

[51] Int. Cl.$^7$ ........................................................ G06K 9/00
[52] U.S. Cl. ........................ 382/133; 382/128; 250/461.2
[58] Field of Search ..................................... 382/128, 304, 382/133–134, 224, 155–159; 348/130, 79–80; 250/461.2, 461.1, 458.1; 600/310, 314, 317, 309; 356/39, 73, 318; 435/40.5, 4–6, 7.21–7.37, 286.1

[56] References Cited

U.S. PATENT DOCUMENTS

| | | | |
|---|---|---|---|
| 3,916,205 | 10/1975 | Kleinerman | 250/461.2 |
| 4,125,828 | 11/1978 | Resnick | 382/134 |
| 4,127,773 | 11/1978 | West | 250/461.1 |
| 4,207,554 | 6/1980 | Resnick et al. | 382/133 |
| 4,293,221 | 10/1981 | Kay et al. | 356/318 |
| 4,354,114 | 10/1982 | Karnaukh | 250/458.1 |
| 4,499,052 | 2/1985 | Krieg | 422/52 |
| 4,700,298 | 10/1987 | Palcic et al. | 382/128 |
| 4,745,285 | 5/1988 | Recktenw | 250/458.1 |
| 4,845,552 | 7/1989 | Jaggi et al. | 382/134 |
| 4,900,934 | 2/1990 | Peeters | 250/461.2 |
| 4,965,725 | 10/1990 | Rutenberg | 382/224 |
| 5,134,662 | 7/1992 | Bacus et al. | 382/133 |
| 5,159,397 | 10/1992 | Kosaka et al. | 356/73 |
| 5,187,749 | 2/1993 | Sugimoto et al. | 382/133 |
| 5,287,272 | 2/1994 | Rutenberg et al. | 382/224 |
| 5,480,804 | 1/1996 | Niwa et al. | 435/286.1 |
| 5,544,650 | 8/1996 | Boon et al. | 660/309 |
| 5,548,661 | 8/1996 | Price et al. | 382/133 |
| 5,663,057 | 9/1997 | Drocourt et al. | 435/40.5 |
| 5,677,966 | 10/1997 | Doerrer et al. | 382/128 |
| 5,733,721 | 3/1998 | Hemstreet, III et al. | 435/6 |
| 6,005,964 | 12/1999 | Reid et al. | 382/133 |

OTHER PUBLICATIONS

Brown et al., J. Clin. Pathol., vol. 37, An Impedance Method, Aug. 31, 1984, 4 pgs.

*Primary Examiner*—Leo H. Boudreau
*Assistant Examiner*—Ishrat Sherali
*Attorney, Agent, or Firm*—Millen, White, Zelano & Branigan

[57] ABSTRACT

A microorganism detecting apparatus comprising a fluorescence microscope section which is furnished with a motor-driven xyz stage assembly for placing thereon a slide sample subject to fluorescent staining. An illumination subsystem for projecting excitation light of predetermined wavelength on the sample and a filter assembly for emission, which limits the band of frequencies emitted to a video camera which captures the images of fluorescent stained microorganisms from the sample slide mounted on the xyz stage assembly. A computer reads the output value of the band-limited signal from the video camera and processes the read output. A subsystem device has controllers which drive the xyz stage assembly so as to permit the microorganism sample to be scanned over its whole area. Each image is displayed on a video display monitor and detected microbes in the sample are stored on a hard drive and in an imaging archive system to permit verification or reexamination.

7 Claims, 2 Drawing Sheets

METHOD OF AND APPARATUS FOR AUTOMATING DETECTION OF MICROORGANISMS

CROSS REFERENCES TO RELATED APPLICATIONS

This application is a continuation-in-part of Ser. No. 08/767,023, filed Dec. 16, 1996.

BACKGROUND

FIELD OF INVENTION

The present invention relates to a method of and apparatus for detecting microorganisms. More particularly, it relates to a microorganism detecting method and apparatus for identifying microorganisms contained on a microorganism sample slide, such as a sample in which the microorganisms are contained in a smear of a body fluid on a microscope slide subjected to fluorescent staining.

Heretofore, microbial tests in utilized in quality control in the manufacturing process of food, beverages, pharmaceuticals and other consumables have relied upon the results of cultures requiring various media, ambient conditions, and other assorted growth requirements. Typically the time required for adequate growth of these cultures is from 48–72 hours. The reliance upon the measurable growth in these cultures by definition delays the process of evaluating the safety of the goods in question, which in turn delays getting products to the consumer, and also increases the cost to the manufacturers as a result of having to hold large inventories for extended periods before being able to release the goods to market.

In view of such circumstances, a large number of rapid measurement methods have heretofore been devised (Misao HARUTA, et el. Simplification. Automation and Speed-up of Food-microbiological Tests. p. 11. Science Forum (1985), and Toshiki MORICHI. New Food Industry. 49 (1989)), but satisfactory methods or apparatuses have not been developed yet. There have been developed. for example an ATP measurement method (Molin, O}. Milsson, L. and Ansehn. S. J. Clin. Microbiol., 18.521 (1983)). an impedance method {Brown. D., Wamer. M. Taylor. C. and Warren, R., J. Clin. Pathol. 37. 65–69 (1984)). an enzyme/fluorescence detecting method (Japanese Patent Laid-open Pub. No. 116700/1983), and a DEFT method in which a membrane filter method and a fluorescence microscope method are combined (G. L. PETTIPHER, UBALDINAM and RODRIGUES, J. Appl. Bacterol., 53. 323 (1982)). and apparatuses to which these principles are applied are commercially available. However, problems arestill left in points of accuracy and rapidity. More specifically, the rapid measurement methods presently in practical use exhibit, at the utmost, accuracies of 102–104microorganisms/mi. One day is usually required for one microorganism to reach this germ density. Another difficulty is that the running costs of culture grounds, reagents etc. are high.

Recently, an apparatus wherein microorganisms are automatically detected rapidly by a fluorescence detecting method subjecting the microorganisms to fluorescent staining has been proposed (Japanese Patent Laid-open Pub. No. 53447/1988). Studies have been done to put the apparatus into practical use as ones of the more rapid instruments to detect microbes. Microscopic foreign matter, has autofluorescence and exist in significant concentration in the natural world. The above mentioned apparatus simultaneously detects both foreign matters and microorganisms. Consequently, in the test of microorganisms contained in a sample to be inspected, such as meat, foul or beverage the problem of accurate assessment of true concentration of microbial contamination cannot be resolved by visual inspection under a fluorescence microscope. Accordingly, the most important issue to resolve in providing an automated method and apparatus for detecting fluorescing microorganisms is the accurate discrimination between microbes and artifacts.

The prior art offered by Niwa et al., in U.S. Pat. No. 5,480,804 addresses a method of and apparatus for detecting microorganisms. Like the current invention, it too suggest the value of fluorescent staining the microbes, but offers a means of detection that depends on the photoelectric conversion fluorescence of a specified wavelength while filtering out noise ascribable to the autofluorescence of artifacts, and basically automatically maps the signal outputs representing the microbes on the sample, without any reliance on imaging microorganisms.

The closest known prior art is called the Dynamic Microscope Image Processing Scanner (DMIPS), U.S. Pat. No. 4,700,298. This device is classified as an image scanner which relies upon a microscope. Unlike its predecessor, the present invention uses a proprietary integrated optical/electronic system for image acquisition rather than a standard microscope. Unlike it predecessor, the invention uses a computer driven autofocus mechanism using a high precision stepping motor to drive the optical/electronic image sensor in the z axis that is integrated with the x,y plane displacement for scanning provided by the precision motorized stage.

(DMIPS) utilizes an analog-digital converter in its image sensor, rather than a simple digital system with no analog components. Image processing in the prior art (DMIPS) relies upon edge detecting algorithms, whereas the current invention uses filters to eliminate all signals but those produced by the desired objects for analysis. In addition, unlike the prior art, the current invention utilizes a trained knowledge based software engine supplied with a complete image data base of microorganisms as well as artifacts, which permits the current invention to actually quantitate and confirm the numbers and positions of microbes detected within a sample utilizing actual images of the microbes. The prior art does not include a robotic specimen handling mechanism, automated changeable light sources, automated lens changing capability, automated condenser operation or automated excitation and emission filter assemblies, nor automated archiving of results.

OBJECTS AND ADVANTAGES

Accordingly, several objects and advantages of the present invention solve the problems mentioned above. The present invention provides a microorganism detecting apparatus combining a fluorescence microscope and a computerized imaging device automates the scanning of a microorganism and archives the information. The invention automatically scans the microorganism, and simultaneously processes the image's signal values and also verifies the position of the Image of the detected microorganism.

More specifically, the microorganism detecting apparatus, according to a first aspect of the present invention, comprises a fluorescence microscope section which is furnished with a mechanical subsystem comprised of a specimen cassette assembly, a pick and place assembly, and motor-driven xyz stage assembly on which a microorganism sample subjected to fluorescent staining may be placed. The system includes an illumination subsystem with three light sources for projecting excitation light of predetermined wavelength on to the sample and a means for filtering light passing to the sample. An imaging subsystem, with a means for detecting and imaging the fluorescence of specified wavelength from the microorganism sample, has a video camera attached to the optical subsystem. The optical subsystem has means to filter light passing to the camera so that only chosen frequencies ascribable to the emission frequency of a specified fluorochrome from said stained sample pass to the camera. A computer, with image capturing and processing means, reads an output from said detection means and processes the read image. The computer has automatic inspection means for driving said stage to permit the microorganism sample to be scanned over its whole area, and for storing each detected image to permit verification.

Further, the present invention has for its object optical discrimination between fluorescent-stained microorganisms and any auto-fluorescent foreign matter. It is intended to provide a microorganism detecting method and apparatus in a second aspect, accomplishing the object with an intelligent image processing software/image database trained to distinguish between fluorescing microbes and auto-fluorescing foreign matter.

More specifically, the microorganism detecting method, according to a second aspect of the present invention, is a method of detecting microorganisms wherein the microorganisms, contained in a microorganism sample subjected to fluorescent staining, are sensed by a trained intelligent image analysis system.

With the microorganism detecting apparatus in the first aspect of the present invention, the fluorescent-stained microorganism sample is placed on the stage of the fluorescence microscope section, and the light from the light source is projected on the microorganism sample. Then, the fluorescence is radiated from the microorganism sample. After passing through the microscope section, the fluorescent image of the microorganism is imaged by the camera. Then it is presented to the intelligent image processing software. The presentation of the image is based on the reference training and the image data base which defines the parameters of morphology, density and brilliance within the specified wavelength.

Owing to the resolution provided by the optics and the image capturing/processing hardware, and the use of filters, the individual microorganisms are accurately detected, and the radiated fluorescence is reliably detected and imaged, even when it has a low intensity due to a small number of microorganisms contained in the sample.

Based on scanning and image processing algorithms programmed into the system's integrated controllers, the following tasks are accomplished: scanning of the microorganism sample over the whole area; the capturing of fluorescent images from the microorganism sample; the processing of image data, based on reference to a trained knowledge-based system loaded with all pertinent image databases of appropriate microbial morphology; and the verifying of the image detection position.

With the microorganism detecting apparatus in the second aspect of the present invention, the fluorescent-stained microorganisms in a sample are set at the predetermined position of the fluorescence microscope section, and they are irradiated with the excitation light of one wavelength or are successively irradiated with the excitation lights of two or more wavelengths. Then, fluorescences are emitted from the sample of the microorganisms.

The fluorescences of various wavelengths and/or specified wavelengths are sensed and convened into the images by the detection means, including the operation of the entire scanning/image processing algorithm under each wavelength of fluorescence, which is specified by the sequential utilization of specific optical filters corresponding to the expected emission frequencies of selected fluorochromes. Under each emission frequency, operation of the scanning/image processing algorithm assures proper identification of all fluorescing microbes. Further, since each optical filter and illumination frequency is associated with fluorochrome-stained organisms specifically contained within the image data bases and for which the knowledge-based system has been trained, discrimination between microbe and foreign matter is assured.

Still further objects and advantages will become apparent from a consideration of the ensuing description and accompanying drawings.

Figure 1:
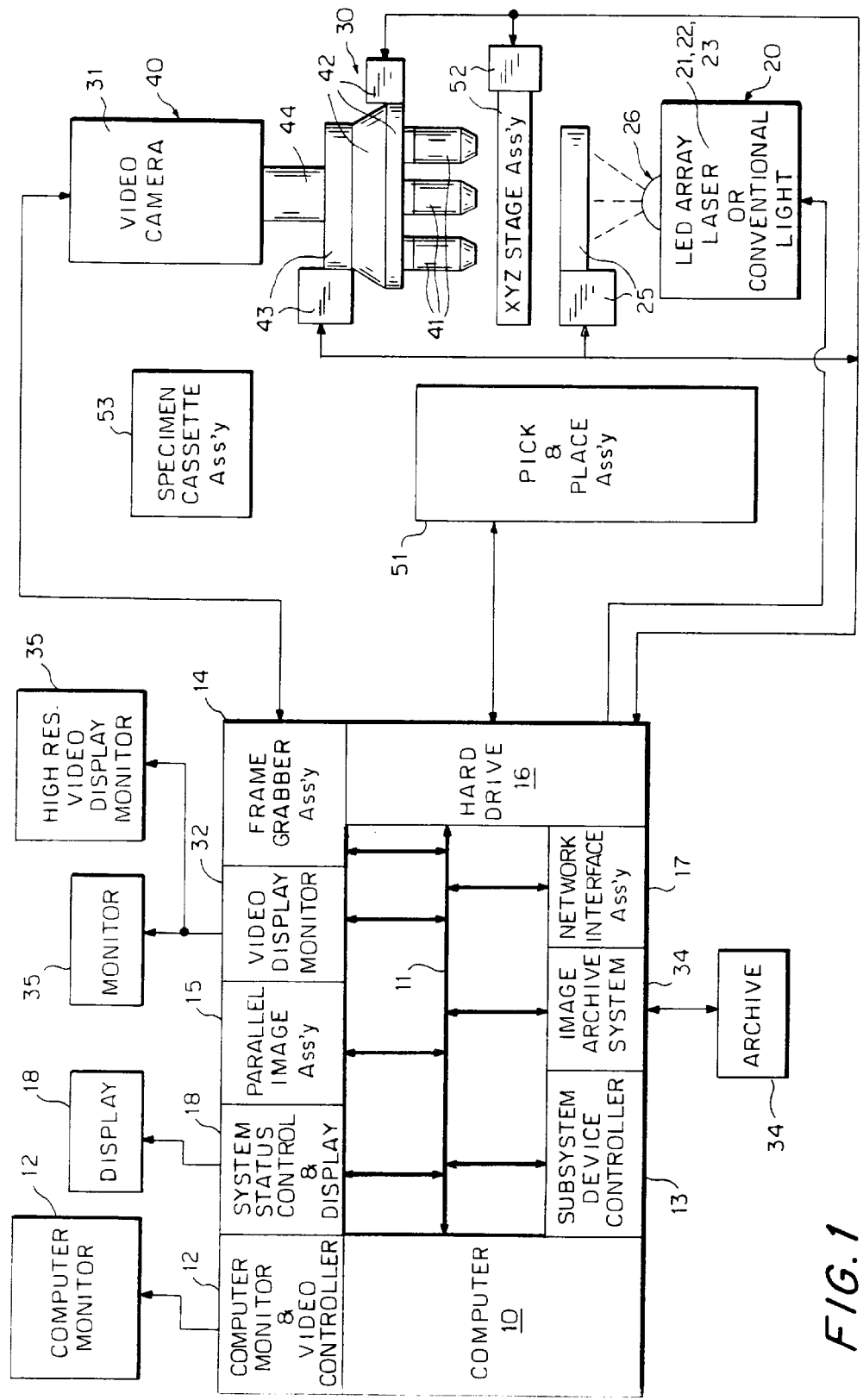
FIG. 1 is a block diagram illustrating a detecting or measuring apparatus of first embodiment of the present invention.

REFERENCE NUMERALS 10 computer
11 standard peripherals
12 computer monitor and video controller
13 subsystem device controllers
14 frame grabber assembly
15 parallel image assembly
16 hard drive
17 network interface assembly
18 system status controller and display
19 system bus and data path
20 illumination subsystem
21 laser
22 LED array
23 conventional light
24 fiber optics assembly
25 filter assembly for excitation
26 condenser lens assembly
30 imaging subsystem
31 video camera
32 video display monitor
33 film recorder
34 imaging archive system
35 high resolution video display monitor
40 optical subsystem
41 objective lens
42 objective lens turret assembly
43 filter assembly for emission
44 optical tube assembly
50 mechanical subsystem
51 pick and place assembly
52 xyz stage assembly
53 specimen cassette assembly

SUMMARY

The detecting apparatus of the present invention constructed as stated below, uses a computer to control the functions of its various subsystem devices, such as its pick and place assembly. The pick and place section picks a specimen slide, film or plate containing fluorescently-stained microorganisms from its specimen cassette assembly and places it on an xyz stage assembly. The subsystem device controllers cause the sample to be illuminated and scanned by the microscope section, which relays the emission of light to the video camera and computer. Light emission, at a specific wavelength, from one of three light sources is directed by a fiber optic assembly through filter assembly for excitation and a condenser lens assembly to a sample slide. The sample emits light at a specific frequency to an objective lens through a filter assembly for emission and an through optical tube assembly to a video camera which captures the fluorescing images from the sample slide and transmits that image to the computer. The computer displays, analyzes and records the image and its coordinates. The sample may include viruses such as the AIDS virus or hepatitis virus.

PREFERRED EMBODIMENT

DESCRIPTION

A microorganism detecting apparatus, according to the first aspect of the present invention, is an automatic inspection apparatus which has the construction as described above. The basic principle of the apparatus is to measure microorganisms in such a way that the means for discriminating between foreign matter and fluorescent-stained microbe is accomplished by an expert-trained system with appropriate image databases of fluorescent microbes and variations of foreign matter. The illumination sources and optical filters assure the delivery and passage of only the light of specified frequency and wavelength. The steps of the microorganism measurement are automatically carried out by an integrated processor. The methods and apparatus of the invention may be employed to detect infectious agents, such as for example, bacteria of all types, animal viruses, plant viruses, prions and bacteriophage. Animal viruses that may be detected include, for example, DNA viruses such as Parvoviruses, Papovaviruses, Adenoviruses, Herpesviruses, Poxviruses, Hepatitus B-like Viruses and RNA viruses such as Picornaviruses, Caliciviruses, Astroviruses, Flaviviruses, Coronaviruses, Paramyxoviruses, Rhabdoviruses, Filoviruses, Influenza Viruses, Arenaviruses, Reoviruses, and Retroviruses. Specifically, viruses that cause disease in animals may be detected using methods of the invention, including, for example, the HIV virus. Plant viruses that may be detected include, but are not limited to, Potyviruses, Luteoviruses, Gemini viruses, Tospoviruses, Criniviruses, Closteroviruses, and Satellite viruses.

The fluorescent-stained microorganism sample for use in the measuring apparatus, according to the present invention, should preferably be one in which microorganisms in an object (for example, a drink, water or air) are caught on a membrane filter having a suitable pore size and then stained with a fluorescent material (for example, fluorescein diacetate (preferred), propidym iodide, fluorescein isothiocyanate, acridine orange, or ethidym bromide). If necessary, the microorganisms are cultured for a short time and then subjected to the staining. Microorganisms can also be detected from a conventional microscope slide as in a smear of body fluid or an histologically-prepared tissue section.

Figure 2:
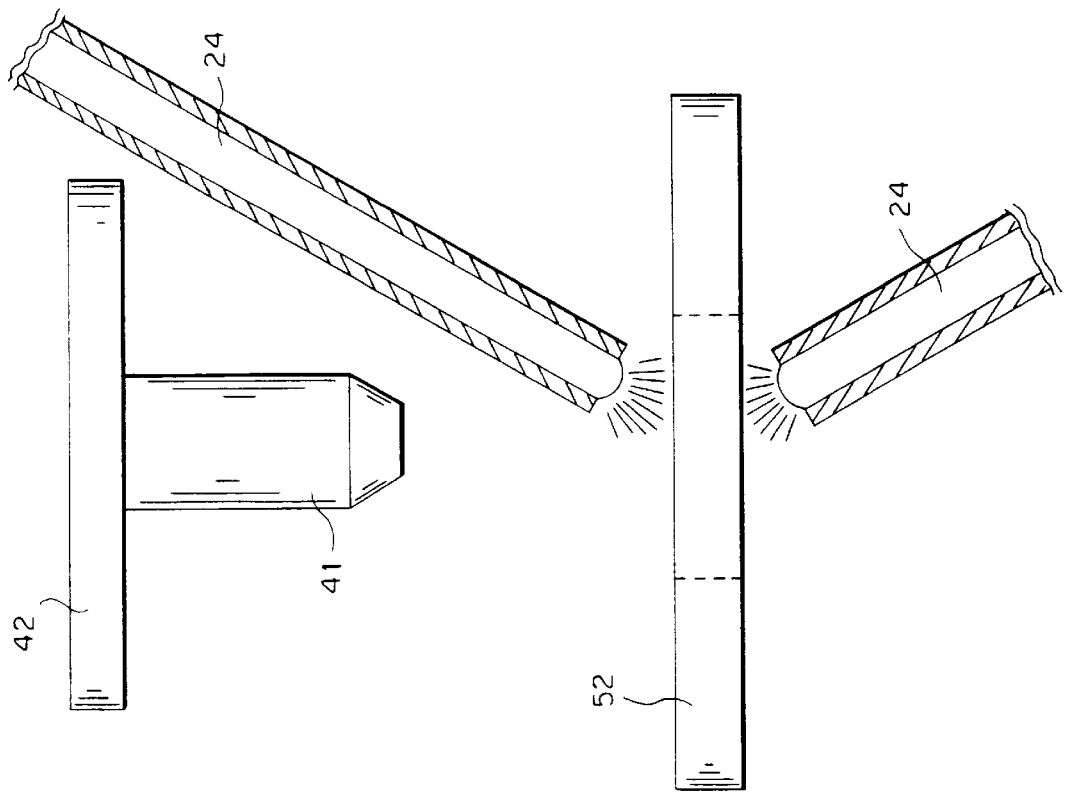
FIG. 2 is side view of an example of the fundamental construction of microscope/imaging section included in the detection apparatus of FIG. 1, utilizing a fiber optic conveyance of specific excitation frequency light from either laser or wave length specific LED light source.

The preferred embodiment of the detection apparatus, according to the present invention, is shown in FIGS. 1–2. The apparatus, displayed in FIGS. 1–2, is comprised of five subsystems: the computer 10, illumination subsystem 20, imaging subsystem 30, optical subsystem 40 and the mechanical subsystem 50. The mechanical subsystem 50 is comprised of a pick and place assembly 51, xyz stage assembly 52, and specimen cassette assembly 53, which are operated by the subsystem device controllers 13. The pick and place assembly 51 operates on an x, y and z plane with two arms. The specimen cassette assembly 53 holds up to 100 standard slides and has ridged sections designed to hold each slide suspended approximately ¹⁄₁₀ inch from each other in a vertical manner. A microorganism sample, subjected to fluorescent staining, is placed on a slide, which is then placed in the specimen cassette assembly 53, which is then placed on a platform. The pick and place assembly 51 is instructed by the subsystem device controllers 13 to pick up the sample slide at the appropriate coordinate in the specimen cassette assembly 53. Commands for the subsystem device controllers 13 can be input manually through the standard peripherals 11 (keyboard, joystick or mouse ) and/or automatically by pre-programed software. The robotic arms, which are flat, slide underneath the sample slide and secure the sample slide by suction onto the flat plate of the arm. The arm of the pick and place assembly 51 then removes the sample slide from the specimen cassette assembly 53 and places the sample slide on the xyz stage assembly 52. The subsystem device controllers 13 automate and synchronize the application of suction to both secure and release the slides at the appropriate time.

The xyz stage assembly 52 is motorized for moving the sample slide underneath the imaging subsystem 30 and above the illumination subsystem 20. A sample is subjected to fluorescent staining, and the illumination subsystem 20 provides a light source means (including laser 21, LED array 22, or conventional light 23 sources depicted in FIGS. 1 and 2) for projecting excitation light of predetermined wavelength on the sample; the fluorescent image of specified wavelength from the microorganism sample is captured by the imaging subsystem 30. The imaging subsystem 30 consists of high resolution video display monitor 35, film recorder 33, and imaging archive system 34 which receives signals from the a video camera 31. The video camera 31 is attached to the optical tube assembly 44 of the optical subsystem 40. The optical subsystem 40 consists of an optical tube assembly 44 that is connected to the motorized objective lens turret assembly 42 containing three objective lens 41 (which are rotated by the motorized objective lens turret assembly 42), and a filter assembly for emission 43 which is attached above the objective lens turret assembly 42. The filter assembly for emission 43 serves as means for limiting the band of frequencies to the selected emission frequencies passed through the optical tube assembly 44 to the video camera 31. The video camera 31, suitable for low level illumination, "sees" the image from the objective lens 41 through the filter assembly for emission 43 and optical tube assembly 44 and transmits that image to the computer 10 subsystem.

The computer subsystem is comprised of a computer 10 (PC) which consists of the standard peripherals 11, computer monitor and video controller 12, subsystem device controllers 13, a frame grabber assembly 14, a parallel image assembly 15, a hard drive 16, a network interface assembly 17, a system status controller and display 18, a system bus and data path 19, and is loaded with software to perform the image capture/image functions for reading and processing the output value of the band-limited signal from the video camera 31. The computer 10 automatically records the coordinates of imaged fluorescent microorganisms, using its subsystem device controllers 13 for each of the moveable components depicted in FIG. 1, which include the pick and place assembly controller, xyz stage assembly controller, light source controller, filter controllers, objective lens controller and frame grabber assembly 14. The computer 10 directs the controllers to scan over the whole surface of each microorganism sample at selected magnifications, using either conventional light 23, laser 21 or LED array 22 as a light source. The computer 10 also automatically stores captured images of the sample and their coordinates, thereby permitting, upon review of the results, the confirmation of the presence or absence of the fluorescent microbes (refer to FIG. 1). The computer also displays the images on a high resolution video display monitor 35 or prints images by film recorder 33 or by transmitting the images to a remote computer monitor and video controller 12 for review of results by the operator, through a network.

The illumination subsystem 20 projects a light source, such as a white light LED array 22, to the motor-driven xyz stage assembly 52 on which the microorganism sample is placed; a filter assembly for excitation 25 selects the excitation wavelength that is passed from the light source through the condenser lens assembly 26 to the sample. The objective lens 41 and the filter assembly for emission 43 are disposed in an optical path extending from the illumination subsystem to the stage, and the filter assembly for emission 43 selects the specified wavelength of the fluorescence that is emitted from the sample by the projection of the excitation light from the illumination subsystem 20 through the sample. The video camera 31, electronically captures the fluorescing image of the microorganism sample which has passed through the filter assembly for emission 43 at the selected frequency.

The apparatus, according to the present invention, uses a video display monitor 32 for observing the real-time display of the imaged microbes which may comprised as shown in FIG. 1. The computer 10 has the automatic fluorescence inspection function and discriminates between artifactual auto- fluorescence and fluorescing microbes.

PREFERRED EMBODIMENT

OPERATION

The operation of the measuring apparatus according to the present invention is as explained in the following: First, a microorganism sample, in which microorganisms have been subjected to fluorescent staining, is removed from the specimen cassette assembly 53 by the robotic pick and place assembly 51, and placed on the xyz stage assembly 52. In this case, the microorganism sample is fixed on a standard slide glass. Conventional light 23, or white light LED array 22 emitted from the illumination subsystem 20 is first passed through the condenser lens assembly 26, then through the filter assembly for excitation 25 which selects the correct entering excitation light wavelength (e.g., 490 nm if the staining agent for the microorganism sample is fluorescein diacetate) to present to the sample. If the laser 21 light source is selected, the light is presented to the sample via the fiber optics assembly 24. The subsystem device controllers 13, controlled by the computer 10, operate the xyz stage assembly 52 in a sliding fashion to allow the whole area of the sample to be scanned.

When the light of the appropriate excitation wavelength passes through the sample, causing the microorganisms in the sample to emit fluorescence, both excitation and emission wavelengths of light convey the image of the sample through the objective lens 41. Next the light passes through the filter assembly for emission 43, which selects the proper emission wavelength for the specific fluorochrome used to stain the sample to be passed to the video camera 31. For example, a filter is selected to exclude all wavelengths except light of 530 nm if the staining agent of the microorganism is fluorescein diacetate.

The reflected or transmitted fluorescent light is sensed and converted into an image by the video camera 31. The image is input to the video frame grabber assembly 14, the video display monitor 32 and is then conveyed high resolution video display monitor 35, while the digitized image of the resulting data is recorded on to hard drive 16 of the computer 10. When the fluorescence from the microorganism sample has been imaged and recorded in this way, the movement position of the xyz stage assembly 52 (a scanned position in the microorganism sample a at this time) is loaded in the hard drive 16 by the subsystem device controllers 13, and the image's position in the microorganism sample is stored in the hard drive 16.

The basic operations as stated above are continuously performed over the whole area of the microorganism sample. Accumulations of image data items (number of positive events) with the images read by the imaging archive system 34 are processed by the computer 10, whereby the total number of the images of fluorescent substances, and the map of the image's positions, are indicated on the video display monitor 32. After the image data items have been output, the function of the computer 10 for vexing the signal positions is actuated, whereby xyz stage assembly 52 stops at the respective positions. Here, the operator of the measuring apparatus verifies the microscopic images of the fluorescent substances with the image display in real-time on the video display monitor 32 to discriminate the microorganisms from the other fluorescent substances. The unnecessary images of the other fluorescent substances can be deleted manually on the computer 10. The measurement image items can be filed and stored on the hard drive 16 or imaging archive system 34, and the file can be drawn out and referred to under the management of the computer 10 at will, as may be needed.

Conclusions, Ramifications, and Scope

Accordingly, it can be seen that the invention simplifies and adds efficiency to the task of detecting microorganisms by providing an improved method and apparatus described in detail above for identifying and quantitating microorganisms on a sample slide, film or plate. A microorganism sample (such as food, beverage, air, water, etc.), is caught on a membrane filter, smeared on a slide (body fluid), or plated on growth media film (from beef, fowl, or other food and food handling surfaces). The current invention employs, sophisticated integrated subsystems varying illumination sources, filter systems, optical system, electronic image recording, and image processing hardware and software to assure rapid and efficient visual discrimination between truly fluorescing microorganisms and autofluorescent foreign matter. It utilizes trained artificial intelligent software, armed with complete representative image databases of both representative microorganisms and foreign matter, while automating the process of quantifying microbial concentrations in particular sample volumes with real-time direct visual verification of recorded image data.

Although the description above contains many specificities, these should not be construed as limiting the scope of the invention, but as merely providing illustrations of some of the presently preferred embodiments of the invention. Various other embodiments and ramifications are possible within its scope. For example, the format of the current invention is applicable to microbial detection requirements for many industries, including (but not limited to) environmental monitoring of air and water for microbial contaminants; food and beverage quality control; procedures to assure acceptable levels of microbes in products; and medical diagnostic procedures, such as the inspection of samples derived from body fluids and tissue.

Another example is in the case of environmental monitoring systems, where water and/or air samples are continuously passed through filters. In the current invention these filters could be inspected at intervals by the method and apparatus for microbial detection.

In the case of food and beverage quality control, samples obtained from meat, fish, fowl, and dairy products could be plated onto media coated film, incubated and inspected by the method and apparatus of the current invention at designated intervals. Results which are obtainable very early in the growth of the microbes found in these samples could lead to projections of the microbial concentrations of the original sample. This could be accomplished by first creating an image data base characterizing growth curves and microbe population dynamics under standardized conditions. With proper training, the knowledge-based software, by referring to these data bases could, within a few hours of initiating the culture, project the population density expected of the sample from these data bases at 24, 48, and 72 hours by the process of extrapolation. Even though products could be released based on these early projections, cultures would continue to grow and be inspected at intervals as insurance against erroneous projections. With proper tracking of products released to market, immediate recall of released products could still be activated, should an error in projection occur to prevent distribution to consumers.

Conclusions as to the safety of the substance being tested could be reached in a very small fraction of the time currently spent waiting for the cultures to mature sufficiently to reach a final determination by methods and apparatus of prior art. The results of applying the current invention in these circumstances would be to improve the safety to consumers, reduce costs for the producers through inventory reduction, and shorten the holding time before releasing foods to market, thereby actually increasing product availability to the consumer.

In the case of medical diagnostic applications, to date there is no prior art providing a rapid and efficient automated method and/or apparatus to systematically read samples suspected of microbial infection (such as Tuberculosis) derived from body fluid, such as sputum, serous drainage, urine sediment, or from issue sections of biopsy material. The current invention provides the method and apparatus to automate the arduous, time-consuming and subjective task of systematically scanning TB smears and tissue sections that have been stained with fluorescent dyes, such as Auramine/Rhodamine or Acradine orange. High volume hospitals have to process as many as hundreds of smears and tissue sections a day. The current invention provides a rapid means to identify and exclude all negative slides that are devoid of microbes (usually 95% of samples), while identifying, verifying, quantitating and recording the positive samples. These positive samples may have as few as one fluorescent microorganism on the entire slide or, on the other extreme, have so many organisms as to be uncountable under prior art.

Additionally, whereas the prior art forces technicians to perform their analyses, fully attired to operate safely in a Level 3 bio-hazard lab (gloves, gown, mask, cap, etc.), manually handling potentially dangerous material, the remote feature of the current invention permits a one-time manual cassette-loading operation of all slides to be analyzed, and then permits the technician to operate the system from the safety and comfort of another room, not in the bio-hazard laboratory.

Thus the scope of the invention should be determined by the appended claims and their legal equivalents, rather than by the examples given.

What is claimed is:

1. An apparatus for detecting and imaging fluorescent substances in a microorganism sample wherein the microorganism sample includes viruses, the apparatus comprising:

a. a stage for placing thereon a microorganism sample subjected to fluorescent staining, and for transporting the sample to permit the same to be scanned;

b. an illuminator for projecting excitation light of a predetermined wavelength onto the sample to fluoresce the sample so that a fluorescent light is emitted from the sample, wherein a predetermined wavelength is selected to fluoresce truly fluorescing microorganisms to distinguish truly fluorescing microorganisms from autofluorescent foreign matter;

c. an emission filter of a predetermined frequency bandwidth for filtering the fluorescent light from the sample, the frequency bandwidth being selected to include the selected emission frequency of the illuminator;

d. an image subsystem including video camera for sensing the filtered fluorescent light conveying the morphology, size and density which has passed through the filter assembly to obtain an actual image of the sample;

e. a frame grabber assembly for capturing and processing the actual image of the sample to produce a band-limited digitized image signal;

f. a parallel image processor assembly for comparing the band-limited digitized image signal to digitize image signals stored in trained knowledge-based software having an image database of selected images of organisms and artifacts in order to determine if the fluorescing image is that of a selected organism or an artifact; and g. data storage for maintaining archives of the images and locations of fluorescing microbes in processed samples.

2. An apparatus according to claim 1, wherein the image subsystem includes appropriate optics and digital imaging device for photoelectric conversion of the fluorescent light.

3. An apparatus according to claim 1, wherein the microorganism sample is a sample in which the microorganisms are caught on a membrane filter and then subjected to the fluorescent staining or are present on opaque growth media film.

4. An apparatus for detecting microorganisms in a microorganism sample subjected to fluorescent staining, comprising:

a. a stage for placing thereon a microorganism sample subjected to fluorescent staining and for transporting the sample to permit the sample to be scanned;

b. an illuminator for projecting excitation light of a predetermined wavelength onto the sample and including a first filter assembly for excitation to select and transmit only light of a predetermined wavelength which flouresces truly fluorescing microorganism to distinguish truly fluorescing microorganisms from autofluorescent foreign matter, wherein a fluorescent light from the truly fluorescing microorganisms is originated from the sample;

c. an optical subsystem through which the fluorescent light from the sample passes, the optical subsystem including an objective lens delivering both an excitation and an emission bandwidth to an optical tube assembly;

d. a second filter assembly for emission placed in the optical tube assembly by which second filter assembly the excitation bandwidth is excluded allowing only the emission bandwidth to pass;

e. an imaging subsystem including a video camera for sensing the filtered fluorescent light conveying the morphology, size and density which has passed through the second filter assembly to obtain the actual image of the sample;

f. a frame grabber assembly means for capturing and processing the actual image of the samples to produce a band-limited digitized image signal;

g. a parallel image processor assembly for comparing the band-limited digitized image signal to digitized image signals stored in trained knowledge-based software having an image data base of selected images of organisms and auto-flourescent foreign matter in order to determine if the image of the sample is a selected organism or an artifact; and h. data storage for maintaining archives of the images and locations of fluorescing microbes in processed samples.

5. An apparatus for detecting microorganisms according to claim 4, wherein the microorganisms in the sample are caught on a membrane filter and then subjected to the fluorescent staining.

6. The apparatus for detecting microorganisms according to claim 1, where the excitation light laser light.

7. The apparatus for detecting microorganisms according to claim 1, wherein the excitation light is from conventional or LED light sources.

* * * * *